United States Patent [19]
Gordon et al.

[11] Patent Number: 5,518,881
[45] Date of Patent: May 21, 1996

[54] TRANSFECTED CELL LINES EXPRESSING AUTOANTIGENS AND THEIR USE IN IMMUNOASSAYS FOR THE DETECTION OF AUTOIMMUNE DISEASE

[75] Inventors: Thomas P. Gordon, Glenelg; James McCluskey, Hyde Park, both of Australia

[73] Assignee: Flinders Medical Centre, Bedford Park, Australia

[21] Appl. No.: 146,423

[22] Filed: Nov. 2, 1993

[51] Int. Cl.⁶ .......................... C12Q 1/68; G01N 33/53; G01N 33/567
[52] U.S. Cl. ............... 435/6; 435/7.1; 435/7.21; 435/69.3; 435/70.3; 435/240.2; 435/975; 536/23.5
[58] Field of Search .................... 435/6, 7.1, 7.21, 435/7.92, 7.95, 69.1, 69.3, 70.1, 70.3, 172.3, 240.2, 320.1, 975; 536/23.5

[56] References Cited

U.S. PATENT DOCUMENTS 4,751,181  6/1988  Keene .................................. 435/70.1
4,784,942  11/1988  Harley .................................. 435/7

FOREIGN PATENT DOCUMENTS

WO89/09222  5/1989  WIPO.
WO91/17171  11/1991  WIPO.
WO92/20811  11/1992  WIPO.

OTHER PUBLICATIONS

Veldhoven, C. H. A., et al. (1992) "The development of a quantitative assay for the detection of anit–Ro/SS–A and anti–LA/SS–B autoantibodies using purified recombinant proteins", *Journal of Immunological Methods*, 151:177–189.

Huff, John P., et al. (1990) "Insights Into Native Epitopes of Proliferating Cell Nuclear Antigen Using Recombinant DNA Protein Products", *J. Exp. Med.* 172:419–429.

Dickey, Darryl W., et al. (1993) "Presence of Anti––La(SS–B) Is Associated With Binding To The 13–kD Carboxyl Terminus of 60–kD Ro(SS–A) in Systemic Lupus Erythematosus", *Journal of Investigative Dermatology*, 100(4):412–416.

McCauliffe, D. P., et al. (1993) "Molecular characterization of the Ro/SS–A autoantigens", *Journal of Investigative Dermatology*, 100(1):73–79.

Buyon, Jill P., et al. (1994) "Autoantibody Responses to the Native 52–KDa SS–A/Ro protein in Neonatal Lupus syndromes, systemic Lupus Erythematosus and Sjogren's Syndrome", *Journal of Immunology*, 3675–3684.

Itoh, K., et al. (1991) "Protein heterogeneity in the human Ro/SSA ribonucleoproteins: The 52– and 60–kD Ro/SSA autoantigens are encoded by separate genes," *J. Clin. Invest.*, 87:177–186.

Harley, J. B., et al., (1992) "Anti–Ro in Sjogren's syndrome and systemic lupus erythematosus," *Rheumatic Disease Clinics of N. America*, 18:337–358.

Gottlieb, E., et al., (1989) "The RNA binding protein La influences both the accuracy and efficiency of RNA polymerase III transcription in vitro," *EMBO J.*, 8:841–850.

Gottlieb, E., et al., (1989) "Function of mammalian La protein evidence for its action in transcription termination by RNA polymerase III," *EMBO J.*, 8:851–861.

Deutscher, et al., (1988) "Molecular analysis of the 60 kda human Ro ribonucleoprotein," *Proc. Natl. Acad. Sci. USA*, 85:9479–9483.

McNeilage, L. J., et al., (1990) "Mapping of epitopes on the La(SS–B) autoantigen of primary Sjogren's syndrome: identification of a cross–reactive epitope," *J. Immunol.*, 145:3829–3835.

Germain, R. N., et al., (1986) "Analysis of the expression of Class II major histocompatibility complex–encoded molecules by DNA–mediated gene transfer," *Annual Reviews in Immunology*, 4:281–315.

Harmon et al., Arthritis and Rheumatism, vol. 27, No. 2, "The Importance of Tissue Substrate in the SS–A/Ro Antigen–Antibody System". Feb. 1984, pp. 166–173.

Chan et al, Journal of Clinical Investigation, vol. 87, "Molecular Definition and Sequence Motifs of the 52–kD Component of Human SS–A/Ro Autoantigen", Jan. 1991, pp. 68–76.

Rother et al, Clin. Exp. Immunol., vol. 83, "La/SSB Ribonucleo–Protein Levels Increased in Transformed Cells", 1991, pp. 369–374.

McCauliffe et al. J. Clin. invest., vol. 85, "Molecular Cloning, Expression, and Chromosome 19 Localization of Human Ro/SS–A Autoantigen", May 1990, pp. 1379–1391.

Barakat et al, Clin. Exp. Immunol, vol. 89, "IgG antibodies From Patients With Primary Sjögren's Syndrome and Systemic lupus Erythematosus Recognize Different Epitopes in 60–kD SSA/Ro protein", 1992, pp. 38–45.

Slobbe et al, Clin. Exp. Immunol., vol. 86, "Detection and Occurrence of the 60– and 52–kD Ro(SS–A) antigens and of Autoantibodies Against These Proteins", 1991, pp. 99–105.

Thomsen et al., Proc. Natl. Acad. Sci, USA, vol. 81, "Promoter–Regulatory Region of the Major Immediate Early Gene of Human Cytomegalovirus", Feb. 1984, pp. 659–663.

*Primary Examiner*—Christine M. Nucker
*Assistant Examiner*—Laurie Scheiner
*Attorney, Agent, or Firm*—Townsend and Townsend and Crew

[57] ABSTRACT

This invention relates to improved in vitro immunoassay methods for detection of autoantibodies associated with autoimmune disease. More specifically, the invention relates to immunoassay methods which utilize a cell line stably transformed with a nucleic acid expressing an autoimmune antigen. This invention also relates to compositions comprising these cell lines and to kits containing such cell lines.

23 Claims, 8 Drawing Sheets

TRANSFECTED CELL LINES EXPRESSING AUTOANTIGENS AND THEIR USE IN IMMUNOASSAYS FOR THE DETECTION OF AUTOIMMUNE DISEASE

TECHNICAL FIELD OF THE INVENTION

This invention relates to improved in vitro immunoassay methods for detection of autoantibodies associated with autoimmune disease. More specifically, the invention relates to immunoassay methods which utilize a cell line stably transformed with a nucleic acid expressing an autoimmune antigen. This invention also relates to compositions comprising these cell lines and to kits containing such cell lines.

BACKGROUND OF THE INVENTION

Autoimmune diseases are those immune system disorders characterized by production of antibodies that react with antigens of the patient's own tissues. More than 30 autoimmune diseases are presently known; these include many which have received much public attention, including rheumatoid arthritis, multiple sclerosis and systemic lupus erythematosus (SLE). The production of specific autoantibodies is associated with certain autoimmune diseases. For a description of the immune mechanisms and autoantibodies involved in autoimmune disease, See Schwartz, R. S., et al. in *Fundamental Immunology*, Second Edition, Paul, W. E., editor, Raven Press, New York (1989) pp. 819–866, incorporated herein by reference.

Autoimmune diseases can be categorized into organ-specific diseases and systemic diseases. Organ-specific autoimmune diseases affect a single organ, such as the thyroid gland, or a physiological system, such as the neuromuscular system. The autoantigens involved in organ-specific diseases are primarily antigens specific to an organ and may be implicated in the pathology of the disease. For example, autoantibodies to thyroglobulin are observed in autoimmune thyroiditis and appear to be involved in the pathology of the disease. Systemic autoimmune diseases, on the other hand, affect multiple physiological systems. The autoantibodies involved in systemic autoimmune disease are generally reactive with more ubiquitous autoantigens, including a group of antigens found in the nucleus of cells. These latter group of autoantigens include DNA, histones, and a number of ribonucleoproteins. See Schwartz, R. S., et al., supra.

Detection and measurement of autoantibodies is used to diagnose and monitor a number of autoimmune diseases. For example, autoantibodies reactive with nuclear autoantigens are generally measured in the clinical laboratory in the antinuclear antibody (ANA) test. The ANA test is an indirect immunofluorescence test that uses a cell line or tissue section as a source for nuclear autoantigens. Nuclear fluorescence in the ANA test indicates the presence of nuclear autoantibodies. Furthermore, the pattern of fluorescence observed can be correlated with the presence of autoantibodies reactive with specific nuclear antigens.

The ANA test is widely used to detect autoantibodies to nuclear antigens, and is useful in the diagnosis of several systemic autoimmune diseases. However, there are problems associated with the ANA test which limit its diagnostic usefulness. In particular, it is difficult to find cell lines or tissue sources that have sufficiently high amounts of all of the desired nuclear autoantigens. Some nuclear autoantigens are produced at only low levels in cell lines and tissue sources commonly used for ANA testing.

An example of such a nuclear autoantigen is Ro/SS-A. Autoantibodies to Ro/SS-A are associated with SLE, neonatal lupus erythematosus, Sjögren's syndrome and other rheumatic diseases. Measurement of anti-Ro/SS-A autoantibodies is important in the diagnosis of these disorders. Therefore, cell lines that express higher levels of Ro/SS-A or other autoantigens which are normally present in low amounts are needed. For nuclear autoantigens such as Ro/SS-A, it would be particularly useful if a cell line also expressing other autonuclear antigens can be modified to overexpress Ro/SS-A, so that the cell line can be used for an improved ANA test.

SUMMARY OF THE INVENTION

The present invention provides methods of detecting autoantibodies in a biological sample for the detection of, for example rheumatic diseases. The methods comprise contacting the biological sample with a cell line stably transfected with a recombinant expression cassette comprising a nucleic acid encoding an autoantigen, reactive with the autoantibodies, incubating the biological sample with the cell line to form an autoantigen:autoantibody complex, and detecting the autoantigen:autoantibody complex, typically by immunofluorescence.

The autoantibodies may be associated with systemic autoimmune diseases such as systemic lupus erythematosus, neonatal lupus erythematosus, or Sjögren's syndrome. Exemplary antigens include Ro/SS-A (both the 60 kd and 52 kd forms) or La/SS-B.

Also provided are cell lines stably transfected with a recombinant expression cassette comprising a nucleic acid encoding an autoantigen. The transfected cell lines are usually a human cell line, such as HEp/Ro 60 or HEp/Ro 52. A preferred promoter for use in the recombinant expression cassettes is the human cytomegalovirus immediate early promoter. The transfected cell line preferably overexpresses the autoantigen to improve sensitivity of the assay.

The invention further provides kits for detecting autoantibodies in a biological specimen comprising a cell line stably transfected with a recombinant expression cassette comprising a nucleic acid encoding an autoantigen, as described above. Exemplary cell lines are HEp/Ro 60 and HEp/Ro 52.

DEFINITIONS

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies are typically tetramers of immunoglobulin molecules. The antibodies may exist in a variety of forms including, for example, Fv, $F_{ab}$, and $F(ab)_2$, as well as in single chains (e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., *Immunology*, Benjamin, N.Y., 2nd ed. (1984), and Hunkapiller and Hood, *Nature*, 323:15–16 (1986), which are incorporated herein by reference).

The term "epitope" refers to the binding site of an antibody. Epitopes are defined by the sequences but are also defined functionally by the ability of one antibody to bind and block the binding of a second antibody to that same site.

This is routinely achieved by competitive immunoassays and is termed epitope mapping.

The term "autoantibody" as used herein refers to an antibody obtained from an individual or animal and which is reactive to a normal cellular antigen(s) from the same individual or animal. The production of autoantibodies is generally associated with autoimmune disease. Autoimmunity and the production of autoantibodies in human autoimmune disease is discussed in detail in Schwartz, R.S., et al., supra.

The term "autoantigen" as used herein refers to an antigen present in normal individuals which is reactive with an autoantibody. Examples of autoantigens include both organ-specific antigens such as thyroglobulin and ubiquitous cellular antigens such as DNA, histones, and ribonucleoprotein particles. A description of known autoantigens and their role in autoimmune disease is described in Schwartz, R. S., et al., supra.

The term "nuclear autoantigen" as used herein refers to an autoantigen that is present in the nucleus of the cell. Autoantibodies reactive to nuclear autoantigens are generally associated with systemic autoimmune diseases, such as SLE and Sjögren's syndrome. Nuclear autoantigens include DNA, histones and a number of ribonucleoproteins. See Schwartz, R. S, et al., supra.

The terms "Ro/SS-A antigen" or "Ro/SS-A autoantigen" refer to particular nuclear autoantigens. Ro/SS-A antigen is a 60 kd protein associated with small RNA molecules, Y1–Y5, which are found in both the nucleus and the cytoplasm. There is also a related 52 kd protein. Autoantibodies to the 52 kd Ro/SS-A protein are closely associated with autoantibodies to the 60 kd Ro/SS-A protein. The above terms refer to both the 60 kd protein and the 52 kd protein and to ribonucleoprotein complexes containing these proteins. The terms "60 kd Ro/SS-A antigen", "60 kd Ro/SS-A autoantigen" or "60 kd Ro/SS-A protein" refer specifically to the 60 kd protein or ribonucleoprotein complexes containing this protein. The terms "52 kd Ro/SS-A antigen", "52 kd Ro/SS-A autoantigen" or "52 kd Ro/SS-A protein refer to the 52 kd protein or ribonucleoprotein complexes containing this protein. Autoantibodies to the Ro/SS-A antigen are associated with both SLE and Sjögren's syndrome. See Itoh, K., et al. (1991) *J. Clin. Invest.* 87:177–186, Chan, E. K., et al., (1991) *J. Clin. Invest.* 87:68–76, and Harley, J. B., et al. (1992) *Rheumatic Disease Clinics of N. America* 18:337–358, all incorporated herein by reference, for a description of the structure of the Ro/SS-A antigen and its association with autoimmune disease.

The terms "La antigen" "La autoantigen" or "La/SS-B antigen" refer to a nuclear autoantigen which contains a RNA polymerase III transcription termination factor expressed in the nucleus and capable of ATP-dependent melting of RNA/DNA hybrids. See Gottlieb, E. et al. (1989) *EMBO J.* 8:841–850 and Gottlieb, E., et al., *EMBO J.*, 8:851–861, both incorporated herein by reference, for a detailed description of the structure and function of the La antigen. The terms "La protein" or "La molecule" refer to the above described RNA polymerase III transcription termination factor. The La protein is associated with a variety of small RNAs including the precursors of cellular 5S RNA and tRNA, 7s RNA, and small cytoplasmic RNAs associated with the Ro/SS-A autoantigen. Autoantibodies to the La autoantigen are associated with both Sjögren's syndrome and SLE.

"Biological sample" as used herein refers to any sample obtained from a living organism or from an organism that has died. Examples of biological samples include body fluids and tissue specimens.

"Nucleic acids" as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Nucleic acid probes" may be DNA or RNA fragments. DNA fragments are prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference.

The term "overexpresses" or "overexpression" as used herein refers to an amount of protein expression that is greater than that which occurs naturally. For example, a transfected cell line is said to overexpress a particular protein if it expresses a greater amount of the protein than is expressed in the nontransfected parent cell line. This generally occurs if the cell line is transfected with a nucleic acid capable of expressing the particular protein molecule. For example, as described in Examples 1–3 herein, transfection of a HEp-2 cell line with a cDNA expressing the 60 kd Ro/SS-A antigen resulted in expression of the 60 kd Ro/SS-A antigen in an amount that was markedly greater than that found in the parent HEp-2 cells.

When referring to an autoantigen expressed by a transfected cell line, overexpression may be measured by titering a series of antisera against both the untransfected parent cell line and transfected cell line in an indirect immunofluorescence assay as described in examples 2 and 3 herein. Overexpression refers to an amount of autoantigen expressed in the transfected cell line that yields a titer at least 8-fold greater than that observed for the parent cell line when the experimental protocol of Example 2 is followed. More preferably, an increase in titer of at least 16-fold is observed; yet more preferably an increase in titer of at least 32-fold is obtained; more preferably an increase in titer of at least 64-fold is observed and most preferably, an increase in titer of at least 128-fold or greater is obtained. See Table 1 for an illustration of the measurement of the increase in titer of a series of autoantisera to determine overexpression of the Ro/SS-A autoantigen.

The term "recombinant expression cassette" refers to a recombinant DNA fragment operably linked to a promoter (which is either constitutive or inducible), suitable for ligation into an expression vector. The recombinant DNA fragment generally encodes a protein or a fragment of a protein. For example, a recombinant expression cassette may contain a DNA or cDNA molecule encoding a particular autoantigen protein.

The phrase "cell culture" refers to the containment of growing cells derived from a multi-cellular plant or animal which allows for the cells to remain viable outside the original plant or animal. The term "cell line" refers to a line of cells that are cultivated in cell culture. The term includes both immortalized cell lines and primary (nonimmortalized) cell lines.

The term "human cell line" refers to a cell line derived from human tissue and composed of human cells. The term "Hep/Ro 60" refers to a HEp-2 cell line that has been stably transfected with a nucleic acid encoding the 60 kd Ro/SS-A antigen. The term "HEp/Ro 52" refers to a HEp-2 cell line that has been stably transfected with a nucleic acid encoding the 52 kd Ro/SS-A antigen.

DESCRIPTION OF THE PREFERRED EMBODIMENT

The present invention relates to improved in vitro immunoassay methods for detection of autoantibodies associated with autoimmune disease. These immunoassay methods utilize cell lines that are transfected with nucleic acids expressing various autoantigens. Methods are described herein for the transfection of cell lines with isolated nucleic acids encoding autoantigens. Methods are also described for the detection of autoantibodies by a variety of immunoassay procedures which utilize the transfected cell lines.

A. Isolation of Nucleic acids Encoding Autoantigens

In order to develop a transfected cell line to express a particular autoantigen, it is first necessary to isolate a DNA or cDNA molecule encoding the autoantigen. The DNA encoding the autoantigen can then be incorporated into a suitable expression vector and transfected into a cell line to induce expression of the autoantigen by the cell line.

As described above, there are a variety of different autoantibodies associated with different autoimmune diseases. See Schwartz, R. S., et al. supra for a discussion of autoantibodies and autoantigens associated with autoimmune disease. There are various methods of isolating DNA sequences encoding autoantigens. Techniques for nucleic acid manipulation of genes encoding these polypeptides such as subcloning nucleic acid sequences encoding polypeptides into expression vectors, labelling probes, DNA hybridization, transfection of cells and the like are described generally in Sambrook, et al., *Molecular Cloning—A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook, et al."

Those of skill in the art are knowledgeable in the various methods of isolating DNA and cDNA molecules encoding autoantigens. In brief, nucleic acid sequences encoding an autoantigen can be isolated by probing a genomic or cDNA library. Genomic or cDNA libraries are prepared generally as described in Sambrook, et al.

There are a variety of methods for probing genomic or cDNA libraries. Nucleic acid probes are often used, particularly if there is DNA sequence information available for nucleic acids encoding the autoantigen protein. For example, the DNA is isolated from a genomic or cDNA library using labelled oligonucleotide probes specific for sequences in the DNA. Restriction endonuclease digestion of genomic DNA or cDNA containing DNA sequences encoding an autoantigen can be used to isolate the DNA encoding these proteins. The DNA sequences encoding a variety of autoantigens are known (See Schwartz, R. S., et al., *supra*). In these cases, a panel of restriction endonucleases can be constructed to give cleavage of the DNA in the desired regions. After restriction endonuclease digestion, DNA encoding an autoantigen is identified by its ability to hybridize with nucleic acid probes, for example on Southern blots, and these DNA regions are isolated by standard methods familiar to those of skill in the art. See Sambrook, et al.

The polymerase chain reaction can also be used to prepare DNA encoding an autoantigen. Polymerase chain reaction technology (PCR) is used to amplify nucleic acid sequences of autoantigen polypeptides directly from mRNA, from cDNA, and from genomic libraries or cDNA libraries. Appropriate primers and probes for amplifying DNA encoding an autoantigen are generated from analysis of the DNA sequences. In brief, oligonucleotide primers complementary to the two 3' borders of the DNA region to be amplified are synthesized. The polymerase chain reaction is then carried out using the two primers. See *PCR Protocols: A Guide to Methods and Applications* (Innis, M., Gelfand, D., Shinsky, J. and White, T., eds.), Academic Press, San Diego (1990). Primers can be selected to amplify the entire regions encoding a full-length autoantigen protein or to amplify smaller DNA segments as desired.

Oligonucleotides for use as probes are chemically synthesized according to the solid phase phosphoramidite triester method first described by Beaucage, S. L. and Carruthers, M. H., 1981, Tetrahedron Letts., 22(20):1859–1862 using an automated synthesizer, as described in Needham-VanDevanter, D. R., et al., 1984, *Nucleic Acids Res.*, 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The sequence of the synthetic oligonucleotide can be verified using the chemical degradation method of Maxam, A. M. and Gilbert, 1980, in W., Grossman, L. and Moldave, D., eds. Academic Press, New York, Methods in Enzymology, 65:499–560.

A variety of expression cloning methods employing probes or assays for the expressed proteins may also be used to isolate nucleic acids encoding autoantigens. Expression cloning methods may be used with expression libraries. For example, a cDNA population can be ligated into vectors designed to permit transcription and translation of the cDNA coding region. The desired cDNA clone may then be identified by immunological screening with an antibody or antiserum that recognizes the desired protein. A variety of immunological screening methods using expression cloning are known to those of skill in the art. See Sambrook, et al. Immunological screening methods are particularly useful for isolating nucleic acids encoding autoantigens because of the availability of the autoimmune antisera or specific antibodies for use in screening.

Other methods known to those of skill in the art may also be used to isolate nucleic acids encoding autoantigens. See Sambrook, et al. for a description of other techniques for the isolation of DNA encoding specific protein molecules.

B. Transfection of Isolated Nucleic Acids Expressing Autoantigens into Cell Lines The expression of nucleic acids encoding autoantigens in cell cultures will typically be achieved by operably linking the gene or cDNA to a promoter (which is either constitutive or inducible), and incorporating into an expression vector. The vectors are suitable for replication and integration in the desired cell lines. The particular promoter used in the construct is not critical to the invention, any strong promoter can be used to produce stable transfectants suitable for use in the invention. Exemplary promoters include promoters derived from the human cytomegalovirus, metallothionine promoter, SV-40 early promoter, SV-40 later promoter, murine mammary tumor virus promoter, Rous sarcoma virus promoter, polyhedrin promoter, or other promoters shown effective for expression in eukaryotic cells. Typical expression vectors contain transcription and translation terminators, initiation sequences, and promoters useful for regulation of the expression of DNA encoding autoantigens. The vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. The vectors preferably contain a marker to provide a phenotypic trait for selection of transformed host cells such as conferring resistance to antibiotics such as ampicillin or neomycin.

Isolated DNA or cDNA molecules encoding autoimmune antigens can be ligated to various expression vectors for use in transforming cell cultures. See Sambrook, et al., *supra* for a description of expression vectors and ligation procedures. The gene sequences to initiate transcription and translation of the DNA sequences encoding the autoantigens are selected to be compatible with the selected host cell. A variety of cloning vectors including those derived from viruses and plasmids may be used. Illustrations of expression vectors suitable for use in mammalian cells are described in examples 1, 4 and 8, herein.

Preferably, mammalian cell lines are used as host cells for transfection. A variety of different cell lines are desirable for transfection by different autoantigens. A list of cell lines readily available is described in ATCC Catalogue of Cell Lines and Hybridomas, 7th Ed. (1992), ATCC, Rockville, Md., USA, incorporated herein by reference. For example, human cell lines such as HEp-2, which are suitable for use in ANA testing, are desirable host cells for transfection with DNA encoding the nuclear autoantigens. These transfected cell lines may be useful in development of improved ANA tests or tests that complement the ANA test. For instance, the HEp/Ro 60 transfected cell line described in examples 1–3 herein may be useful as improved cell line for ANA testing because it expresses increased levels of the 60 kd Ro/SS-A antigen. This cell line may be useful in an improved ANA test which can more sensitively detect Ro/SS-A autoantibodies. Alternatively, this cell line or other cell lines transfected by DNA expressing the 60 kd Ro/SS-A antigen may be useful in development of a more specific test for R0/SS-A autoantibodies.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells. See Sambrook, et al. for a detailed description of transformation procedures.

The transformed cells are cultured by means well known in the art. *Biochemical Methods in Cell Culture and Virology*, Kuchler, R. J., Dowden, Hutchinson and Ross, Inc., (1977). A variety of immunoassay formats known to those of skill in the art may be used to select transfected cell lines that express or overexpress an autoantigen (see below). Cell lines expressing or overexpressing selected autoantigens due to transfection by a nucleic acid encoding the autoantigen may then be used to develop immunoassays.

C. Immunoassays for Measurement of Autoantibodies

Autoantibodies reactive with a particular protein can be measured by a variety of immunoassay methods. For a review of immunological and immunoassay procedures in general, see *Basic and Clinical Immunology* 7th Edition (D. Stites and A. Terr ed.) 1991. Moreover, the immunoassays of the present invention, which use transfected cell lines expressing particular autoantigens, can be performed in any of several configurations. These immunoassay configurations are reviewed extensively in Enzyme Immunoassay, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, *Antibodies, A Laboratory Manual,* supra, each of which is incorporated herein by reference.

Immunoassays to measure autoantibodies can be either competitive or noncompetitive binding assays. In competitive binding assays, the sample analyte competes with a labeled analyte for specific binding sites on a capture agent bound to a solid surface. Preferably, the capture agent is a transfected cell line overexpressing an autoantigen. For competitive binding assays, the labeled analyte is, for example, a labeled antibody which competes for binding to the autoantigen. The concentration of labeled analyte bound to the transfected cell line is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

A number of combinations of capture agent and labelled binding agent can be used. Preferably, a transfected cell line overexpressing an autoantigen is used as the capture agent and labelled anti-human antibodies specific for the constant region of human antibodies can be used as the labelled binding agent. Goat, sheep and other non-human antibodies specific for human immunoglobulin constant regions (e.g. $\gamma$ or $\mu$) are well known in the art.

Other proteins capable of specifically binding human immunoglobulin constant regions, such as protein A or protein G may also be used as the labelled binding agent. These proteins are normal constituents of the cell walls of streptococcal bacteria. They exhibit a strong non-immunogenic reactivity with immunoglobulin constant regions from a variety of species. See, generally Kronval, et al., *J. Immunol.*, 111:1401–1406 (1973), and Akerstrom, et al., *J. Immunol.*, 135:2589–2542 (1985). The above immunoassays all use a solid phase separation method wherein one of the components of the immunoassay is bound to a solid support. In the above assay formats, the solid support is preferably a transfected cell line that is attached to a suitable solid support such as a microscope slide or a microtiter plate.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3H$, $^{125}I$, $^{35}S$, $^{14}C$, or $^{32}P$ was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Non-radioactive labels may be attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see U.S. Patent No. 4,391,904, which is incorporated herein by reference.

The labeled compounds can be detected by a variety of means. The means for detecting the labeled compound depends on the on the type of label that is used and the format of the immunoassay. For instance, in a indirect immunofluorescence assay, a fluorescent microscope is used. In this type of assay, the transfected cell line is attached to a microscope slide and autoantibodies are bound to autoantigens expressed in the cell line. A fluorescent-labeled binding agent capable of binding to the autoantibodies is then used to visualize the bound autoantibodies under the fluorescent microscope. See Examples 2 and 3 herein for a demonstration of an immunoassay in an indirect immunofluorescent format. The term "immunofluorescence" as used herein refers to both direct and indirect immunofluorescence procedures. Direct immunofluorescence methods are those in which the primary antibodies reactive with the antigen are labeled with a flourophore.

This invention also embraces diagnostic kits for detecting the presence of autoantibodies which comprise a transfected cell line expressing or overexpressing an autoantigen; a container and instructional material for performing the test.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

EXAMPLES

Example 1: Transfection of HEp-2 with cDNA Encoding the Human 60kD Ro/SS-A Antigen a) Gene cloning and constructs

The full length cDNA encoding the 60 kd Ro/SS-A molecule was cloned from a human T-cell line (Hutt-78) cDNA library by screening with a 300 base pair, 5' cDNA probe derived by polymerase chain reaction. The cDNA was sequenced and found to be identical to that described by Deutcher et al. (1988) *Proc Natl Acad Sci USA* 85:9479–9483. For transfection, the cDNA was cloned into a mammalian expression vector under the control of the human cytomegalovirus immediate early promoter (IICMV) (described in Thomsen et al. (1984) *Proc. Natl. Acad. Sci. USA* 81:659–663) and polyadenylation sequences. This expression vector is based on pRc/CMV (Invitrogen, San Diego, Calif.).

b) Transfections

HEp-2 cells (ATCC #LCL23) (Moore, A. F., et al. (1955) Cancer Res. 15:998) were maintained in culture as monolayers in RPMI supplemented with 10% fetal calf serum, non essential amino acids, glutamine, antibiotics and $5 \times 10^{-5}$M 2-mercaptoethanol (complete RPMI). Transfection was carried out by the calcium phosphate precipitation method (See Margulies H., Evans G. A., Ozato K., Camirini-Otero R. D., Tanaka K., Apella E., Seidman J. G. (1983) *J. Immunol.* 130:463– 470). In order to facilitate selection of drug resistant transformants, the selectable marker gene pSV$_2$ neo (See Southern, P. J. and Berg, P. (1982) *J. Mol. Appl. Genet.* 1:327– 341) was co-transfected with the vector containing the 60 kd Ro/SS-A cDNA. Stable transfectants designated HEp-Ro 60 were selected in complete RPMI containing G418 (Gibco, Grand Island, N.Y.) at 0.4 mg/ml, and subsequently cloned by limit dilution prior to analysis for expression of human 60 kd Ro/SS-A.

Example 2: Expression and Intracellular Localization of the 60 kD Ro/SS-A Antigen in Transfected HEp-2 Cells a) Immunofluorescence Cell lines were grown overnight on multi-well slides, then fixed in a mixture of acetone and methanol (3:1) at –20° C. for 2 min, then air dried. 60 kd Ro/SS-A protein was detected by incubation of the monolayers for 30 min with human sera diluted in phosphate buffered saline (PBS), or neat monoclonal antibody (MAb) culture supernatant. Following the PBS wash, the monolayers were incubated with fluorescein isothiocyanate labelled sheep anti-human immunoglobulin or sheep anti-mouse immunoglobulin (Silenus, Australia) diluted 1:100 dilution in PBS. The anti 60 kd Ro/SS-A MAb, 2G10, was a gift from Dr. G. J. M. Prujin (University of Nijmegen, The Netherlands). The anti-La/SS-B MAb, A1, was a gift of Dr. E. M. Tan and has been previously described (See Chan E. K. L.; Tan, E. M. (1987) *J. Exp. Med.* 166:1627–1640). End-point titers were obtained following two-fold serial dilution of sera from 1:100. Normal human sera were screened at a dilution of 1:100. The anti-Ro/SS-A positive sera used in this study were positive for anti Ro/SS-A by counterimmunofluorescence (CIE) and negative for other specificities on CIE and IF-ANA. Other sera included reference sera for Ro/SS-A, La/SS-B, nRNP, Sm, Scl-70 (CDC, Atlanta), PCNA, centromere, mitotic spindle and sera from 20 healthy donors.

Indirect immunofluorescence (IF) staining of HEp-2 and 60 kd Ro/SS-A transfected HEp-2 cells (HEp/Ro 60) revealed typical characteristic nuclear speckling in the HEp-2 cells and a dramatic overexpression of Ro/SS-A in the transfectants (FIG. 1). In the transfectants, the expression was predominantly nuclear in localization, with intense nucleolar staining. Those cells with the highest intensity staining also showed weak cytoplasmic staining detected with anti-Ro/SS-A specific autoantisera. No surface staining of fixed, non-permeabilised cells with MAb or autoantisera with anti-Ro/SS-A specificity was observed (data not shown). The level of overexpression of 60 kd Ro/SS-A varied across the cloned population, giving non-uniform staining intensity ranging from the background level of endogenous Ro/SS-A, to intense staining giving titers of up to 128 fold greater than the endogenous level of expression. HEp/Ro 60 cells with the highest intensity staining made up approximately 10–15% of the population. This variation in the level of expression is thought to be due to the regulation of expression by the HCMV promoter, and has been observed in other transfection systems.

b) Immunoblotting

Whole cell extracts were prepared by lysis of cells at 2×10$^7$/ml in sodium dodecyl sulphate (SDS) sample buffer containing dithiothreitol. After boiling for 3 min., proteins were separated by standard SDS-polyacrylamide gel electrophoresis (SDS-PAGE) on 10% gels. Proteins were transferred to nitrocellulose (Amersham, UK) using a semi-dry transfer apparatus (Novablot, Pharmacia LKB, Sweden). Nitrocellulose filters were blocked for one hour in PBS containing 3% low-fat powdered milk, then incubated for one hour in sera diluted in wash buffer (PBS, 3% powdered milk and 0.5% Tween 20). The nitrocellulose filters were washed five times in wash buffer, then probed with rabbit anti-mouse immunoglobulin (Dako, Sweden) to amplify the signal. Antibody binding was detected using $^{125}$I-Protein A (Amersham, UK) and autoradiography. Prestained molecular weight markers (BioRad, Richmond, Calif.) were used to estimate molecular mass.

Figure 1A:
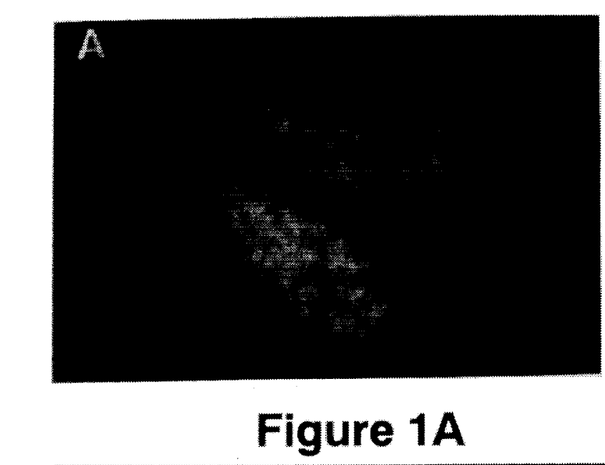
FIG. 1. The 60 kd Ro/SS-A protein is more readily detected in the nucleus of 60 kd Ro/SS-A transfected HEp-2 cells than in untransfected cells by indirect immunofluorescence HEp Ro/60 (A) and HEp-2(B) are stained with Mab 2G10. Hep/Ro 60 (C) and HEp-2(D) are stained with anti 60 kd Ro/SS A reference sera (CDC7) (original magnification× 400).
Figure 1B:
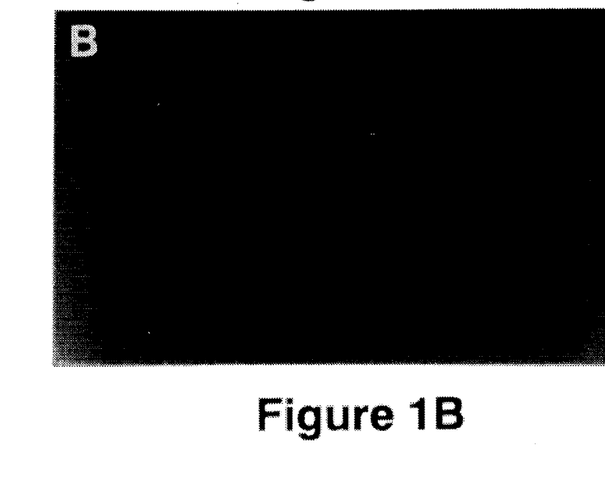
Figure 1C:
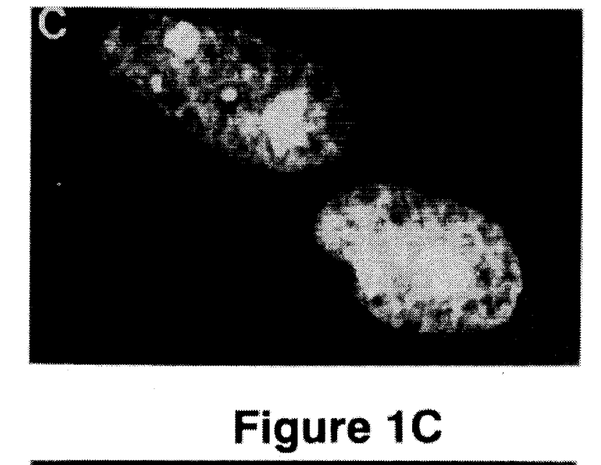
Figure 1D:
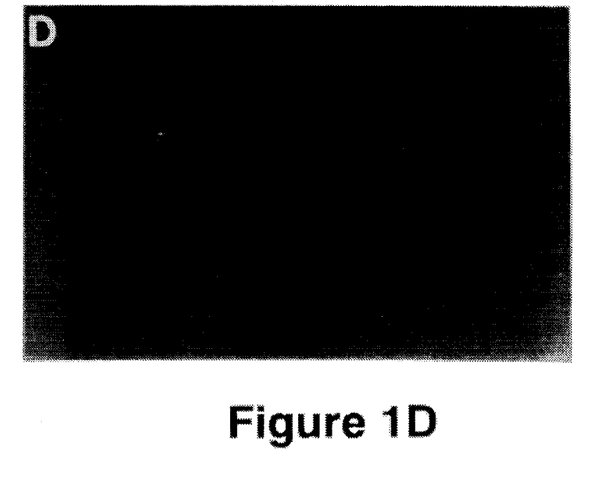
Figure 2:
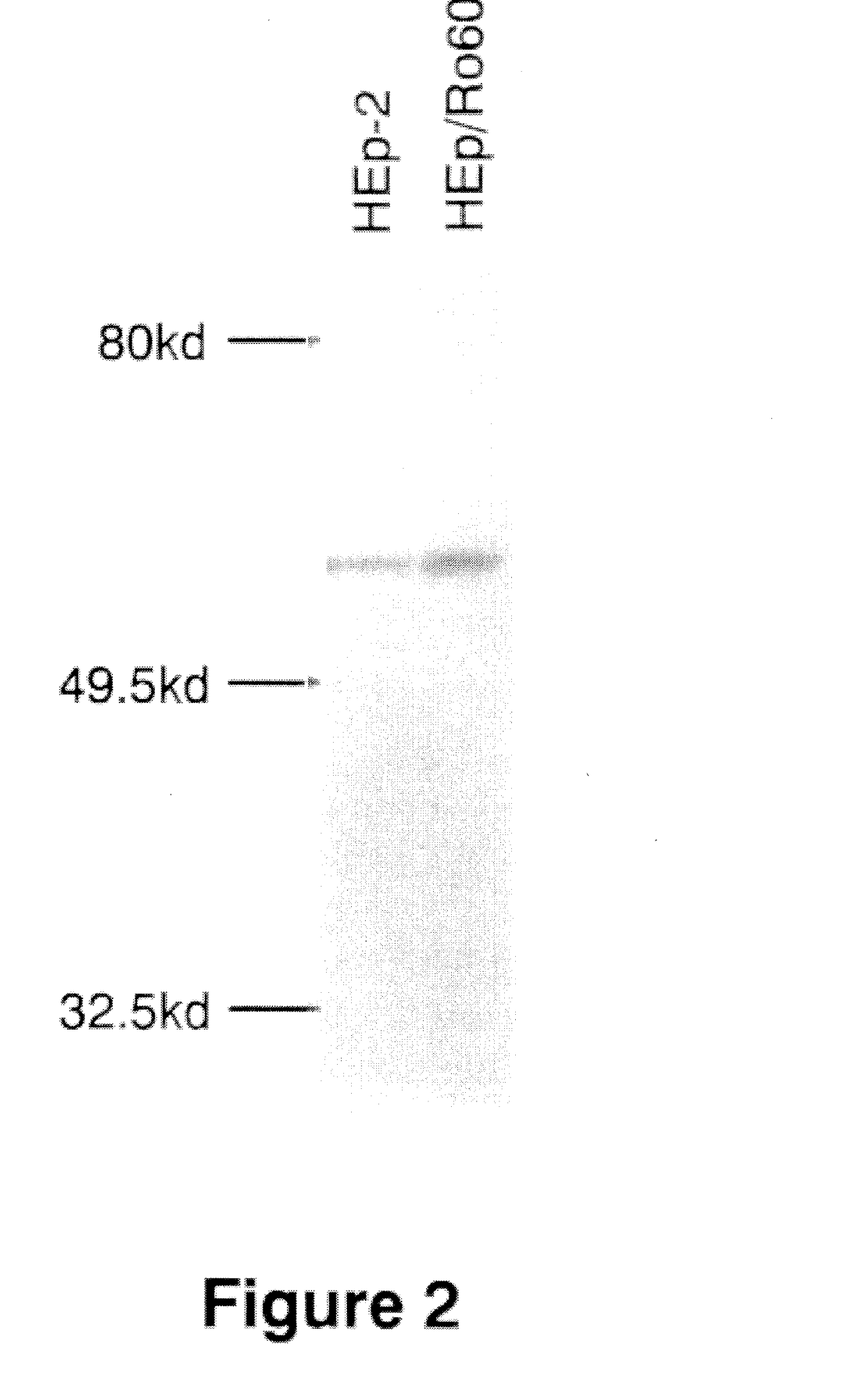
FIG. 2. Immunoblot showing that the transfected Ro/SS-A cDNA is expressed as a 60 kd protein. Cell lysates were transferred to nitrocellulose membrane and probed with a 60 kd Ro/SS-A specific MAb (2G10). Reactivity was detected using $^{125}$-I Protein A and autoradiography.

Western blot analysis of HEp/Ro 60 cells probed with anti-Ro/SS-A specific MAb, 2G10, demonstrated an increase in the level of expression of an immunologically identical 60 kd protein (FIG. 2). The overexpressed Ro/SS-A polypeptide reacts with both monoclonal and polyclonal anti-Ro/SS-A antibodies and has an identical molecular weight to endogenous 60 kd Ro/SS-A. The discrete nuclear speckled pattern on IF coincides with earlier studies which showed that the Ro/SS-A antigen is predominantly nuclear in location. Interestingly, prominent nucleolar staining was also observed implying that the 60 kd Ro/SS-A protein shuttles between the nucleus and nucleolus. Variable cytoplasmic staining was also detected which could represent true cytoplasmic localization, or be due to diffusion of the antigen into the cytoplasm during fixation. Despite overexpression, no Ro/SS-A was detected on the surface membrane of HEp/Ro 60. This is consistent with the finding that mouse cells transfected with human La/SS-B do not express surface La/SS-B under conditions of overexpression, ultra-violet irradiation and serum deprivation as reported by others (see Examples 4 and 5).

Example 3: Immunofluorescence of Human Sera on HEp/Ro 60 Cells and on the HEp-2 Parent Cells Immunofluorescence using HEp/Ro 60 and the HEp-2 parent cells was carried out as described for Example 2. The anti-Ro/SS-A positive sera used in this study were positive for anti Ro/SS-A by counterimmunofluorescence (CIE) and negative for other specificities on CIE and IF-ANA. Other sera included reference sera for Ro/SS-A, La/SS-B, nRNP, Sm, Scl-70 (CDC, Atlanta), PCNA, centromere, mitotic spindle and sera from 20 healthy donors.

Transfected HEp-2 cells were analyzed for their ability to accurately, sensitively and specifically detect 60 kD Ro/SS-A by IF. Twenty-four sera positive for anti-Ro/SS-A on CIE were titered in 2-fold dilutions starting at 1:100, against HEp-2 and HEp/Ro 60 cells (see Table 1). Twenty normal human sera showed no staining on HEp-2 and HEp/Ro 60 cells at 1:100 dilution. The dramatic increase in end point titer of anti-60 kd Ro/SS-A sera was accompanied by a characteristic staining pattern, which enabled the sensitive and specific recognition of anti-60 kd Ro/SS-A protein. The expression of other autoantigens detected by routine IF-ANA was analyzed. No distortion of cells morphology, alteration in localization, or in the level of expression was observed when HEp/60 or the parent cell HEp-2 were stained by IF when reference sera to Sm, Scl-70, PCNA, centromere, mitotic spindle and mAb to La/SS-B (data not shown).

TABLE 1

Indirect immunofluorescence of human anti-Ro/SS-A sera on parent HEp-2 cells and 60 kd Ro/SS-A-transfected HEp 2 cells*

| Sera+ | Titer | | Increase in titer |
|---|---|---|---|
| | Parent HEp-2 | HEp/Ro 60‡ | |
| CD7§ | 400 | 6400 | 16 |
| 1 | 800 | 12800 | 16 |
| 2 | 400 | 12800 | 32 |

TABLE 1-continued

Indirect immunofluorescence of human anti-Ro/SS-A sera on parent HEp-2 cells and 60 kd Ro/SS-A-transfected HEp 2 cells*

| Sera[+] | Titer Parent HEp-2 | HEp/Ro 60[‡] | Increase in titer |
|---|---|---|---|
| 3 | 400 | 51200 | 128 |
| 4 | 400 | 6400 | 16 |
| 5 | 200 | 25600 | 128 |
| 6 | 400 | 6400 | 16 |
| 7 | 400 | 6400 | 16 |
| 8 | 1600 | 25600 | 16 |
| 9 | 1600 | 12800 | 8 |
| 10 | 400 | 25600 | 64 |
| 11 | 400 | 25600 | 64 |
| 12 | 800 | 12800 | 16 |
| 13 | 400 | 6400 | 16 |
| 14 | 400 | 25600 | 64 |
| 15 | 400 | 6400 | 16 |
| 16 | 400 | 6400 | 16 |
| 17 | 400 | 25600 | 64 |
| 18 | 800 | 25600 | 32 |
| 19 | 800 | 51200 | 64 |
| 20 | 800 | 12800 | 16 |
| 21 | 800 | 25600 | 32 |
| 22 | 400 | 6400 | 16 |
| 23 | 400 | 6400 | 16 |

*Cultured cells were fixed in acetone and methanol and incubated on glass slides with 2-fold dilutions of human sera.
[+]Positive for anti-Ro/SS-A on counterimmunoelectrophoresis.
[‡] HEp-2 cells transfected with a CDNA encoding the full-length 60 kd Ro/SS-A.
§ CDC anti-Ro/SS-A reference serum.

Example 4: Comparison of an IFA Utilizing a Transfected Cell Line with an ELISA Method for Detection of Anti Ro/SS-A Autoantibodies The ability of HEp/Ro60 to sensitively and specifically detect 60 kd Ro specific autoantibodies in an IFA assay was compared to commercially available recombinant 60 kd Ro protein in an ELISA format. The production of the HEp/Ro 60 cell line is described in Example 1, herein.

Immunofluorescence was performed as described in Example 1, herein. End point titers were obtained following two-fold serial dilution of sera from 1:100. Normal human sera were screened at a dilution of 1:100.

ELISA assays for detection of anti-Ro antibodies. Microwell ELISA plates (Nunc, Denmark) were coated with recombinant 60 kd Ro (AMRAD, Australia) at IU/well diluted in 0.03 M sodium carbonate buffer, pH 9.6, and were incubated overnight at 4° C. After blocking with 3% bovine serum albumin, the wells were incubated at 37° C. for 1 hr with duplicate samples of serum diluted 1:500 followed by washing with PBS/0.05% Tween 20. Bound IgG was detected using alkaline phosphatase-conjugated anti-human IgG (Sigma, St. Louis, USA) and Sigma 104 phosphatase substrate. Optical density (OD 405 nm) values greater than 3 SD above the mean of 60 normal controls were considered positive.

The anti-Ro positive sera used in this study were positive for anti-Ro autoantibody by counterimmunoelectrophoresis (CIE) and negative for other specificities on CIE and immunofluorescence. Sera from 20 healthy volunteers were used as normal control sera.

Figure 3:
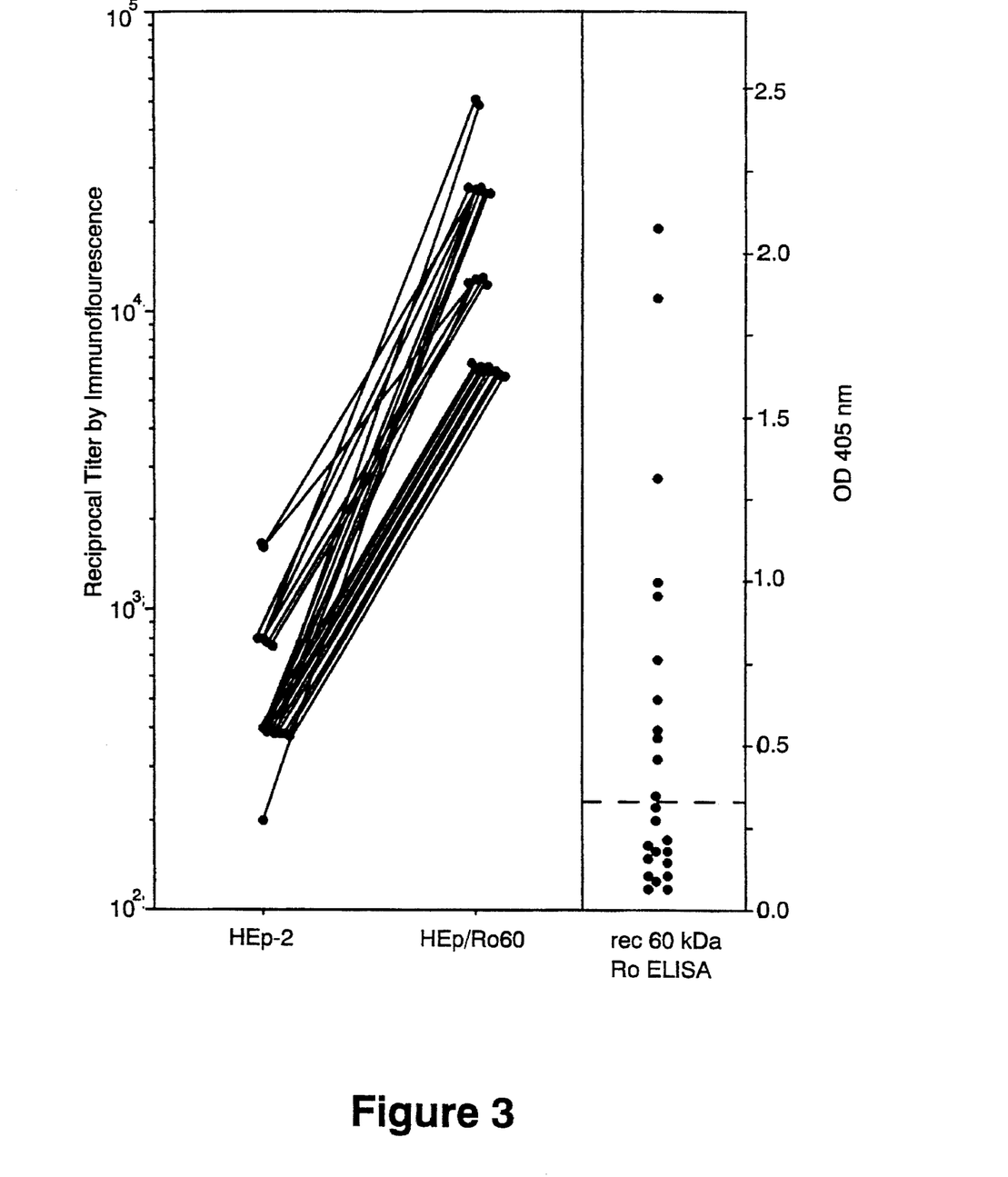
FIG. 3. Comparison of an IFA using HEp/Ro 60 with an ELISA assay. Immunofluorescence and ELISA assays were performed as described in Example 4.

Twenty-four sera positive for anti-Ro on CIE were titerd in two-fold dilutions starting at 1:100, against HEp-2 and HEp/Ro60 cells. These sera were also screened by the recombinant 60 kd ELISA at a dilution of 1:500 (See FIG. 3). Twenty normal human sera showed no staining on the parent HEp-2 or the HEp/Ro60 cells at a 1:100 dilution (data not shown). A dramatic increase in the end-point titer against HEp/Ro60 was demonstrated, indicating the increase in the sensitivity of these transfectants over parent cells to detect 60 kd Ro. The recombinant 60 kd Ro ELISA failed to detect 13 of the 24 sera with known reactivity to native 60 kd Ro protein. The failure to detect anti-60 kd Ro antibody by the recombinant 60 kd Ro ELISA does not correlate with low titer by immunofluorescence on HEp-2 or HEp/Ro60.

This example demonstrates the superior sensitivity of a human cell line transfected with human 60 kd Ro (HEp/Ro60) to detect autoantibodies to 60 kd Ro compared with a recombinant 60 kd Ro ELISA. Sera for this study were selected for their ability to detect native Ro protein by counterimmunoelectrophoresis. The transfected 60 kd Ro is overexpressed in vivo in a eukaryotic expression system where processing, post-translational modification and folding of the protein will produce a functional protein of native structure. In prokaryotic expression systems used to produce recombinant proteins, limited post-translational modifications occur and there is no guarantee that the corrective native conformational folding occurs. The sensitivity of 60 kd Ro to disruption of autoreactive epitopes suggest that many sera react with conformational determinants not present on recombinant proteins.

Example 5: Transfection of HEp-2 with cDNA Encoding the Human 52 kD Ro/SS-A Antigen a) Gene cloning and constructs The full length cDNA encoding the 52 kd Ro molecule was cloned from a human T cell line (Hutt-78) cDNA library by screening with a full-length 52 kd Ro cDNA probe derived by polymerase chain reaction. For transfection, the cDNA was cloned into mammalian expression vector analogous to pRc/CMV (Invitrogen). The plasmid contains the human cytomegalovirus immediate early promoter (HCMV) (Thomsen, D. R., et al. (1984) *Proc. Nat. Acad. Sci.*, USA 81: 659–663) and 3'-polyadenylation sequences. The selectable marker was contained on a separate plasmid.

b) Transfections

HEp-2 cells were maintained in culture as monolayers in RPMI supplemented with 10% fetal calf serum, non-essential amino acids, glutamine, antibiotics and $5\times10^{-5}$M 2-mercaptoethanol (complete RPMI). Transfection was carried out by the calcium phosphate precipitation method as described in Example 1, herein. In order to facilitate selection of drug resistant transformants, the selectable marker gene $pSV_2$ neo (Southern, P. J. and Berg, P., *supra*) was co-transfected with the vector containing the 52 kd Ro cDNA. Transfectants were selected in complete RPMI containing G418 (Gibco, Grand Island, N.Y.) at 0.4 mg/ml, and subsequently cloned by limit dilution prior to analysis for expression of human 52 kd Ro.

Example 6: Expression and Intracellular Localization of the 52 kD Ro/SS-A Antigen in Transfected HEp-2 Cells Immunofluorescence was performed as described in Example 2. The 52 kd protein was detected by incubation of the monolayers for 30 min with human sera diluted 1:100 in phosphate buffered saline (PBS). The anti-Ro positive sera used in this study were positive for anti-Ro by counterimmunoelectrophoresis (CIE) and negative for other specificities on CIE and IF-ANA. Immunoblotting was performed as described in Example 2.

Figure 4A:
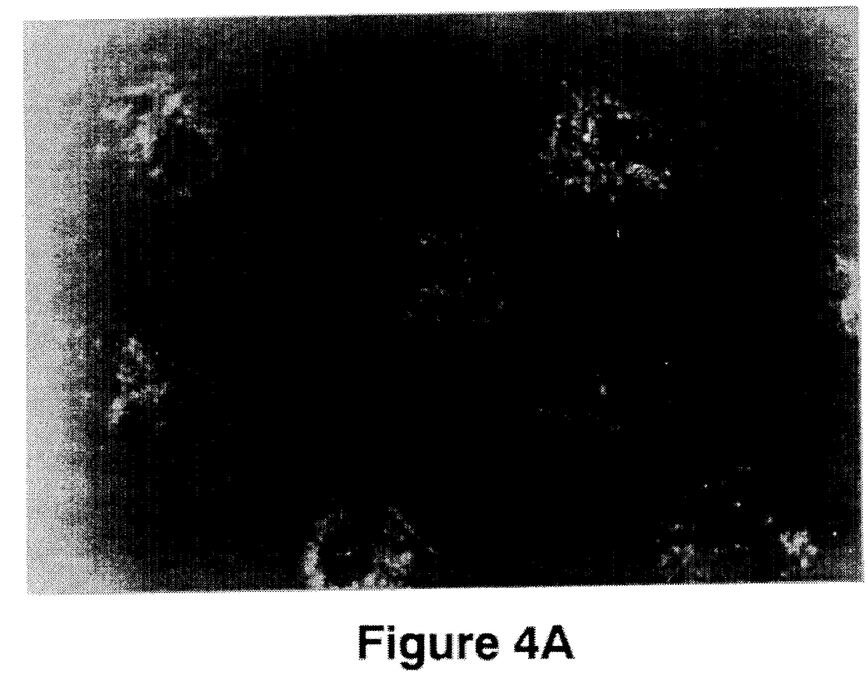
FIG. 4. Immunoflourescence staining of HEp-2 (A) and HEp/Ro 52 (B) with anti-52 kd Ro sera. Immunofluorescence was performed as described in Example 6.
Figure 4B:
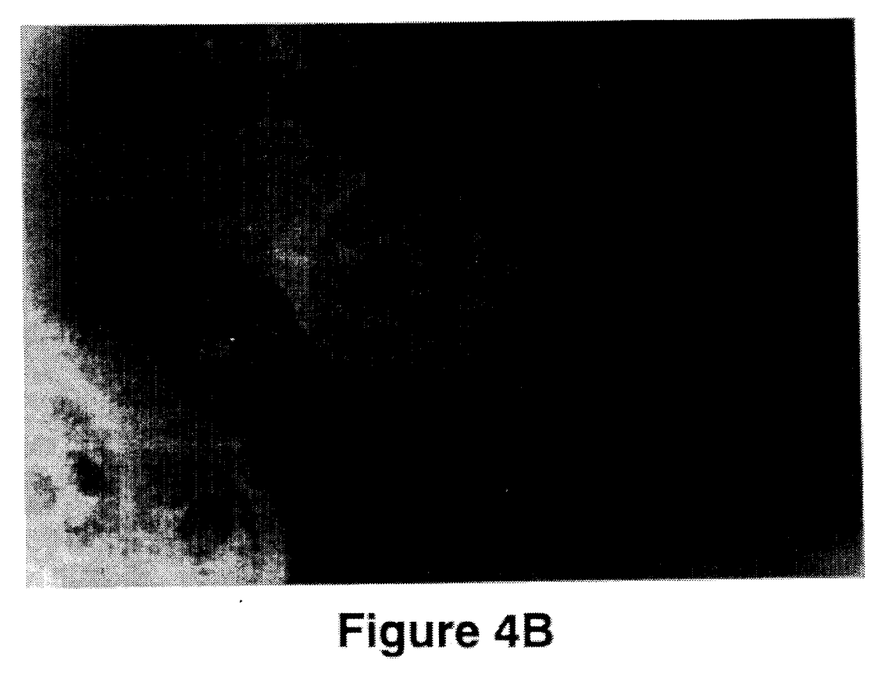

Indirect immunofluorescence staining of HEp-2 and 52 kd Ro transfected HEp-2 (HEp/Ro52) cells with autoantisera positive for the 52 kd Ro protein revealed typical nuclear speckling on the parent cell line, and dramatic overexpression of the 52 kd Ro protein in the cytoplasm of the HEp/Ro52 (FIG. 4). It is difficult to determine from the indirect immunofluorescence whether there is localization in the nucleus of these transfectants as well as the cytoplasm, however, the pattern is predominantly cytoplasmic.

Figure 5:
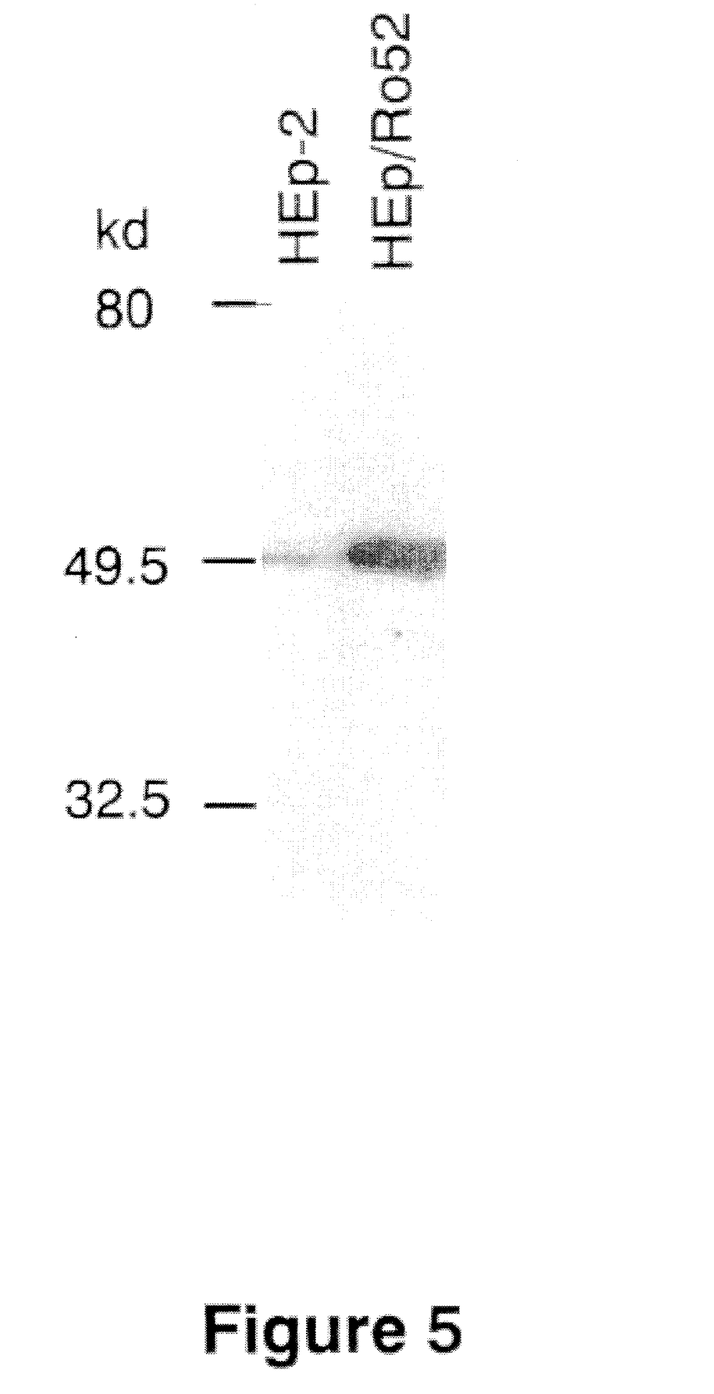
FIG. 5. Immunoblot showing that the transfected Ro/SS-A is expressed expressed as 52 kd protein. Cell lysates were run on 10% SDS-PAGE and transferred to nitrocellulose membranes and probed with autantisera specific for 52 kd Ro/SS-A. Reactivity was detected using enhanced chemiluminescence and flourography.

Western blot analysis of HEp/Ro52 probed with an anti 52 kd Ro antisera revealed a single overexpressed band of apparent molecular mass of 50 kd, co-migrating with the endogenous 52 kd Ro molecule (FIG. 5).

Example 7: Immunofluorescence of Human Sera on HEp/Ro 52 Cells: Comparison with an ELISA assay Immunofluoresence was performed as described in Example 6, herein. The anti-Ro positive sera used in this study were positive for anti-Ro by counterimmunoelectrophoresis (CIE) and negative for other specificities on CIE and IF-ANA.

Full length 52 kd Ro was expressed in *Escherichia coli* as a 6×Histidine (6×His) fusion protein using the pQE vector and the QIA express System (QIAGEN, Calif., USA). Recombinant protein was prepared by metal chelate affinity chromatography in 8M urea according to the manufacturers instructions. Microwell ELISA plates (Nunc, Denmark) were coated with 52 kd Ro-6×His fusion protein or recom- Twenty-three patient sera positive for Ro by counterimmunoelectrophoresis (CIE) were analyzed on the parent HEp-2 and HEp/Ro52 cells by IF for the detection of autoantibody specific for the 52 kd Ro protein. Sera were also analyzed by recombinant ELISA for reactivity against the 52 kd and the 60 kd Ro proteins. Seventeen of the 23 sera were positive for 52 kd Ro by ELISA, of these 13 gave cytoplasmic staining specific for the transfected 52 kd Ro protein in HEp/Ro52 (Table 2). Sera negative for 52 kd Ro by ELISA (60 kd Ro monospecific sera and 10 normal control sera) were negative for 52 kd Ro by IF on HEp/Ro52.

The ability to distinguish the anti 52 and anti 60 kd Ro activities should enable more precise classification and association of these autoantibodies with disease subsets. These transfected cells will provide a simple diagnostic reagent for the verification of the presence of autoantibody to the 52 kd Ro protein.

TABLE 2

Comparison of Immunofluorescence and ELISA to Detect 52 kd Ro

| Sera (1) | rRo60 ELISA (OD 405 nm) (2) | rRo52 ELISA (OD 405 nm) (3) | Ro52 detected by HEp/Ro52 Transfectants (fluorescence above Hep-2) |
|---|---|---|---|
| 1 | − (0.08) | + (0.305) | − |
| 2 | − (0.58) | + (2.000) | +++ |
| 3 | − (0.078) | + (0.622) | − |
| 4 | − (0.134) | + (0.919) | + |
| 6 | − (0.118) | + (2.000) | − |
| 7 | + (1.532) | + (1.912) | +++ |
| 8 | + (0.284) | + (1.507) | + |
| 9 | − (0.203) | + (0.252) | + |
| 10 | − (0.186) | + (0.342) | +++ |
| 11 | − | + (2.000) | +++ |
| 12 | − | + (0.556) | + |
| 13 | − | + (1.414) | + |
| 14 | − | + (1.414) | + |
| 15 | − | + (1.752) | ++ |
| 16 | − (0.22) | + (1.747) | − |
| 17 | − | + (1.752) | ++ |
| 18 | − (0.092) | − (0.053) | − |
| 19 | nd | − (0.073) | − |
| 20 | − (0.144) | − (0.099) | − |
| 21 | nd | − (0.172) | − |
| 22 | nd | − (0.133) | − |
| CDC7 (Ro Ref sera) | + (0.317) | nd | − | nd = not done
(1) Patient sera positive for anti-Ro/SS-A on counterimmunoelectrophoresis
(2) Values 3 standard deviations above the mean of 20 normals were considered positive (OD < 0.250)
(3) Values 3 standard deviations above the mean of 20 normals were considered positive (OD < 0.182)
− No staining observed above endogenous expression
+ Weak cytoplasmic staining
+++ Strong cytoplasmic staining binant 60 kd Ro (IU/well) (AMRAD, Australia) diluted in 0.03M sodium carbonate buffer, pH 9.6, and were incubated overnight at 4° C. After blocking with 3% bovine serum albumin, the wells were incubated with duplicate samples of serum diluted 1:500 and washed with PBS/0.05% Tween 20, and bound IgG was detected using alkaline phosphatase-conjugated anti-human IgG (Sigma, St. Louis, USA) and Sigma 104 phosphatase substrate. Optical density (OD 405 nm) values greater than 3 SD above the mean of 60 normal controls were considered positive.

Figure 6A:
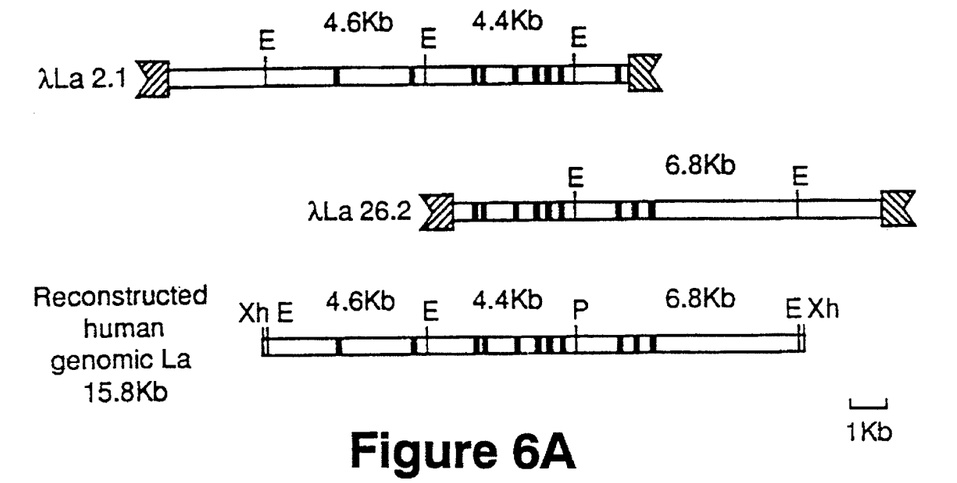
FIG. 6. Gene constructs. (A) Reconstruction of the human genomic La gene. EcoRI fragments of 4.4, 4.6 and 6.8 kb were isolated from two λ phage clones, λLa20.2 and subcloned into the plasmid pGEM-7Zf. During construction of the gene, 40 base pairs of polylinker sequence were introduced into an intron (P). The approximate locations of exons are indicated as solid vertical bars. (B) Human La cDNA clone in the expression vector pEE6/HCMVIGS. Restriction endonuclease sites are indicated as follows: B, BamHI; E, EcoRI; K, Kpul, Xb, XbaI; Xh, XhoI.

Example 8: Transfection of Murine LTA-5 Cells with cDNA and genomic DNA Encoding the Human La (SS-B) Nuclear Autoantigen a) Gene constructions The plasmid, pLa15.8, encoding human genomic La (FIG. 6A) was constructed in four steps form two Charon 3Aλ phage clones, λLa2.1 and λLa26.2 (See Chambers, J. C., et al. *J. Biol. Chem.* 263:18045–18051, which were a gift from Dr. J. Keene. The EcoRI fragments, 4.6 kb, and 6.8 kb, from the phage were subcloned into the cloning vector pGEM-7Z (Promega, Madison, Wis., USA). The 3' EcoRI site of the 4.4 kb subclone was deleted by partial EcoRI digestion and Klenow repair of the DNA ends. The 4.6 kb EcoRI fragment was then cloned in the correct orientation into the 5' EcoRI site of the 4.4 kb subclone. This larger fragment (9.0 kb) was excised by initial digestion of the XbaI polylinker restriction site followed by Klenow repair and ClaI digestion. This 9.0 kb fragment was then directionally cloned into the Klenow repaired BamHI site and ClaI digested polylinker site of the 6.8 kb subclone. The final genomic clone (pLa15.8) contained within the vector pGEM7-Zf, contains 40 base pairs of polylinker sequence introduced between the 4.4 kb and 6.8 kb EcoRI fragments.

Figure 6B:
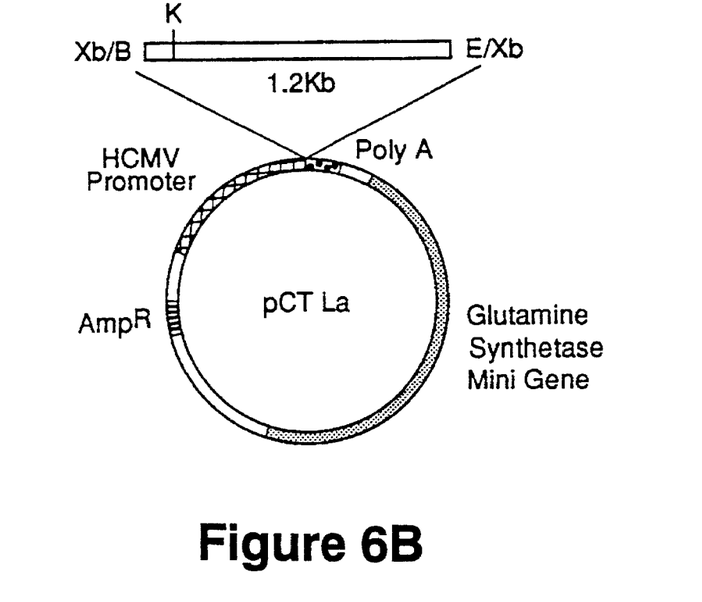

The plasmid, pCTLa (FIG. 6B), encodes a human La cDNA under the control of the human cytomegalovirus immediate early promoter. For this construction, a human La cDNA lacking 90 base pairs of 5' non-coding sequence was first cloned from a polymerase chain reaction product of a full length La cDNA clone (See McNeilage, L. J., et al. (1990) *J. Immunol.* 145:3829–3835). A KpnI/EcoRI fragment containing 1097 nucleotides of the La cDNA was then replaced with the corresponding fragment from the original cDNA clone. The remainder of the reconstructed cDNA clone was sequenced to ensure there were no polymerase chain-reaction derived substitutions. The resulting Klenow-repaired BamHI/EcoRI fragment containing the full length La cDNA was subcloned into a XbaI, Klenow-repaired cloning site of the expression vector pEE6/HCMV/GS (Celltech, UK).

b) Transfections

LTA-5 cells were maintained in culture as monolayers in Dulbecco's modified Eagle's medium (DMEM) supplemented with 10% fetal calf serum, non-essential amino acids, glutamine, antibiotics and $5 \times 10^{-5}$M 2-mercaptoethanol (complete DMEM). Transfection was carried out as described in Example 1, herein. In order to facilitate selection of drug resistant transformants, the selectable marker gene pSV$_2$nco (See Southern, P. J., and Berg, P, (1982) *J. Mol. Appl. Genet.* 1:327–341) was co-transfected with either the reconstructed human La genomic gene (pLa15.8) or the cDNA construct (pCTLa). Transfectants were selected in complete DMEM containing G418 (Gibco, Grand Island, N.Y., USA) at 0.2 mg/ml, and subsequently cloned by limit dilution prior to analysis for expression of human La.

Example 9: Localization and Expression of Human La Antigen in Transfected Murine Fibroblasts a) Immunofluorescence Cell lines were grown overnight on multiwell slides, then fixed in a mixture of acetone and methanol (3:1) at −20° C. for 2 min and then air dried. La protein was detected by incubation of the monolayers for 30 min with human sera or monoclonal antibody (mAb) ascites fluid diluted 1:100 in phosphate buffered saline (PRS), or neat mAb culture supernatant. Following a PBS wash, the monolayers were incubated with a 1:100 dilution of fluorescein isothiocyanate labeled sheep [F(ab)$_2$] anti-human immunoglobulin or sheep [F(ab)$_2$] anti-mouse immunoglobulin (Silenus, Australia). Monoclonal antibodies A1, A2 and A3 were a gift from Dr. E. M. Tan, and SW1, SW3 and SW5 were a gift form Dr. D. Williams and have been previously described (See Chan, E. K. L., et al. (1987) *J. Exp. Med.* 166:1627–1640 and Smith, P. R., et al. (1985) *J. Immunol. Med.* 77:63–76). Human serum with an anti-La activity came from a patient with primary Sjögren's syndrome and also contained activity against the 60 kDa Ro antigen. Serum with anti-60 kDa Ro activity but lacking anti-La specificity came from a patient with systemic lupus erythematosus.

Figure 7:
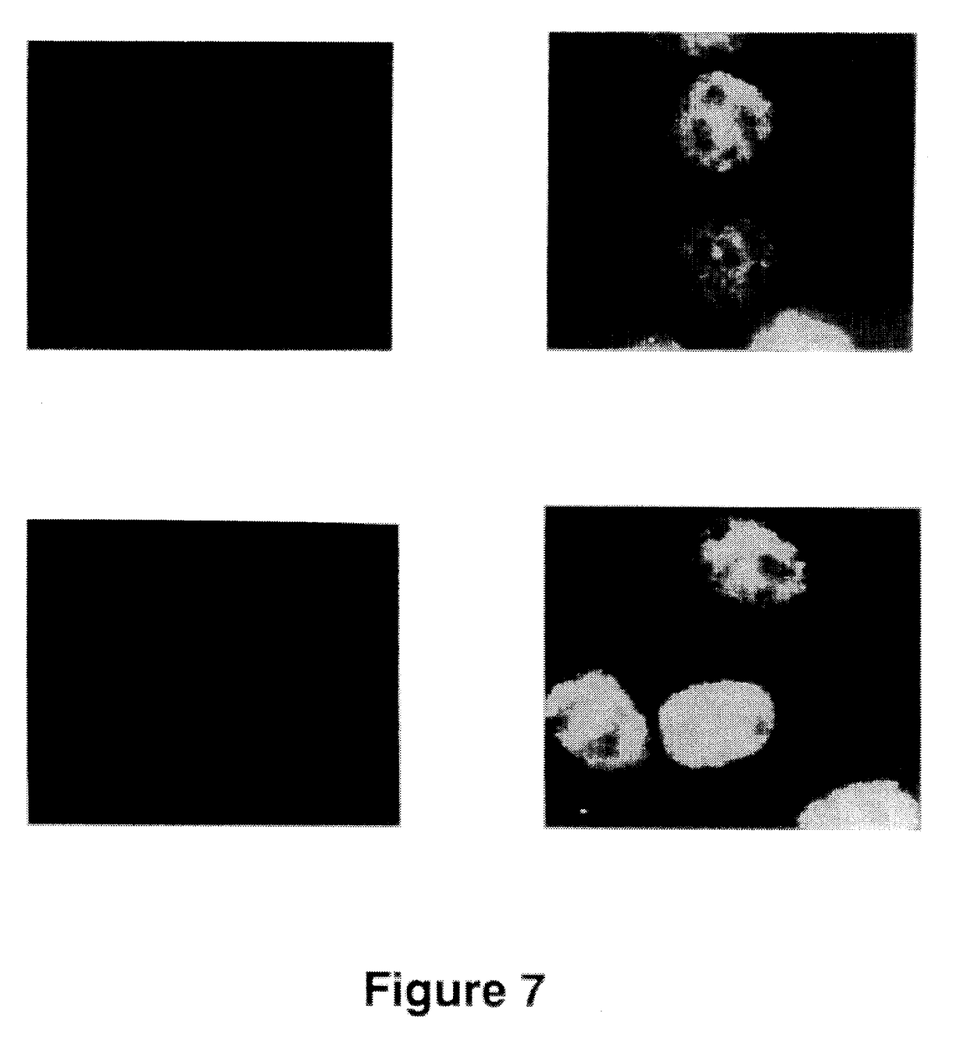
FIG. 7. Nuclear localization of human La expressed in transfected murine fibroblasts. Indirect immunofluorescence staining of the murine fibroblast line LTA-5 transfected with the human genomic La construct (upper right panel) and untransfected LTA-5 (upper left panel) with mAb A1, specific for human La; and staining of untransfected LTA-5 with normal human serum (lower left panel) or a human autantiserum containing anti-La and anti-60 kd Ro activity (lower right panel) demonstrating endogenous mouse La expression. Magnification×400.

Selectable marker genes were co-transfected with either the cDNA or the genomic human La constructs to form stable, drug-resistant transfectants independently expressing these forms of human La. Following culture in selection media, transfected murine fibroblasts were cloned by limit dilution and analyzed by indirect immunofluorescence to determine the localization of the human La protein. Permeablized transfectants stained with specific anti-human La monoclonal antibodies, including mAb A1, predominantly revealed coarse nuclear speckles and fine nuclear granules. Weak, diffuse cytoplasmic staining was also observed. This pattern of La distribution was indistinguishable from that of endogenous murine La stained with patient auto-antibodies crossreactive with murine La antigen. The human La cDNA transfectants and human La genomic DNA transfectants showed an identical immunofluorescence pattern. (See FIG. 7.)

There was no detectable expression of human La protein on the cell surface of untransfected LTA-5 cells or any of the human La-transfectants when examined by indirect immunofluorescence of live-cells by microscopy or by flow cytometry, using anti-human La specific mAbs or patient anti-La autoantisera. Surface expression of human La or endogenous mouse La could not be demonstrated following treatment of these human La-transfectants under conditions reported to induce the surface expression of endogenous La antigen in other cell types. Transfectants were exposed to a wide range of UVB irradiation doses (0, 1, 10, 100 and 500 mJ/em$^2$), and were analyzed by flow cytometry for the expression of surface human La after culture for 1, 4 or 20 hours. Culture in conditions of serum deprivation (0.5% FCS) for 48 h, followed by release from synchronization by the addition of 10% Concanavalin A stimulated T-cell supernatant (Baboonian, C., et al., (1989) *Clin. Exp. Immunol.* 78:454–459) did not result in the induction of surface expression of human or murine La as determined by flow cytometry. Murine fibroblasts may not have all the necessary requirements for the expression of surface La; however, these data suggest that tissue-specific or disease-specific factors, rather than relative overexpression of La, accounts for surface expression observed by others.

b) Immunoblotting

Immunoblotting was performed as described in example 2 herein. More specifically, western blot analysis of La expression in LTA 5 cells transfected with the human genomic (LTA La g1–g3) and human cDNA (LTA-La c1) La genes was carried out. Lysates were transferred to a nitrocellulose membrane and probed with a patient autoantiserum (anti-La serum) which cross reacts with murine La, and with a human La specific mAb, A1 (anti-human La). Reactivity was developed using a peroxidase-coupled second antibody and enhanced chemiluminescence flourography.

Figure 8:
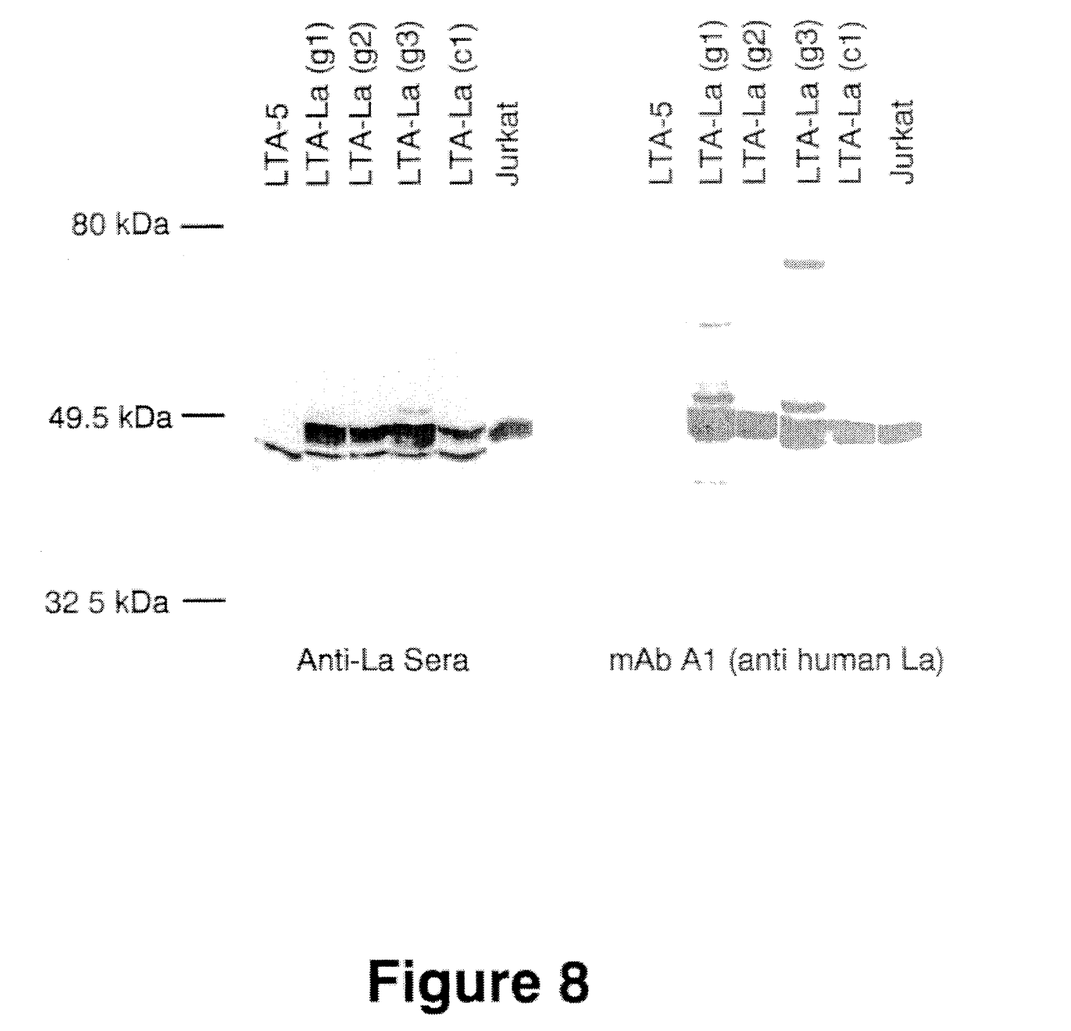
FIG. 8. Expression of human La in transfected murine fibroblasts. Western blot analysis in LTA-5 cells transfected with the human genomic (LTA-La g1–g3) and human cDNA (LTA-La cl) La genes. Lysates were transferred to a nitrocellulose membrane and probed with a patient autoantiseum (anti-La serum) which cross-reacts on murine La, and with a human La-specific mAb, A1 (anti-human La). Reactivity was developed using a perixodase-coupled second antibody and enhanced chemiluminescence.

Western blot analysis demonstrated that human La was of the correct apparent molecular mass in transfected murine cells since it co-migrated with La expressed in human cells and was clearly distinguishable in electrophoretic migration form the endogenous murine La antigen, which runs at a lower apparent molecular mass. The human La antigen expressed in transfected murine fibroblasts reacted with a human autoantiserum and anti-La mAbs specific for human La protein. Human La protein expressed from genomic and cDNA constructs was similar in apparent molecular mass in most clonal isolates (for example, clones g3 and c1). However in some transfectant clones expressing the genomic human La gene product (for example, clones g1 and g2), higher molecular weight protein bands were detected in Western blot analyses. The higher molecular weight forms of human La were detected by several human La-specific mAbs, A1, SW1 and SW3, and to a lesser extent by the patient anti-la antisera. (See FIG. 8.)

It is understood that the examples and embodiments described herein are for illustrative purposes only and that various modifications or changes in light thereof will be suggested to persons skilled in the art and are to be included within the spirit and preview of this application and scope of the appended claims.

What is claimed is:

1. A method of detecting anti-Ro/SS-A autoantibodies in a human biological sample comprising:
   a) contacting said biological sample with cells from a mamalian cell line stably transfected with a recombinant expression cassette comprising a nucleic acid encoding a human Ro/SS-A autoantigen, wherein said autoantibodies are reactive with said Ro/SS-A autoantigen and wherein said transfected mammalian cell line overexpresses said Ro/SS-A autoantigen;
   b) incubating said human biological sample with said cells from said transfected mamalian cell line to form a complex of said autoantibodies bound to said Ro/SS-A autoantigen in said cells; and
   c) detecting said autoantigen:autoantibody complex.

2. A method according to claim 1 wherein said autoantibodies are associated with systemic lupus erythematosus or Sjögren's syndrome.

3. A method according to claim 1 wherein said Ro/SS-A autoantigen is 60 kd Ro/SS-A.

4. A method according to claim 1 wherein said Ro/SS-A autoantigen is 52 kd Ro/SS-A.

5. A method according to claim 1 wherein said mammalian cell line is a human cell line.

6. A method according to claim 5 wherein said human cell line is HEp/Ro 52.

7. The method according to claim 5 wherein said human cell line is HEp/Ro 60.

8. A method according to claim 1 wherein the autoantigen:autoantibody complex of step (c) is detected by immunofluorescence.

9. A method according to claim 1 wherein said recombinant expression cassette further comprises a human cytomegalovirus immediate early promoter.

10. The method of claim 1 wherein the autoantigen:autoantibody complex of step (c) is detected by measuring a labeled binding agent bound to the autoantigen:autoantibody complex.

11. The method of claim 1 wherein said labeled binding agent is a fluorescent-labeled binding agent.

12. The method of claim 11 wherein said fluorescent-labeled binding agent is an antibody.

13. A HEp-2 cell line stably transfected with a recombinant expression cassette comprising a nucleic acid encoding a human Ro/SS-A autoantigen, wherein said transfected HEp-2 cell line overexpresses said Ro/SS-A autoantigen.

14. The HEp-2 cell line according to claim 13 wherein said cell line is HEp/Ro 60.

15. The HEp-2 cell line according to claim 13 wherein said cell line is HEp/Ro 52.

16. The cell line according to claim 13 wherein said recombinant expression cassette further comprises a human cytomegalovirus immediate early promoter.

17. A kit for detecting anti-Ro/SS-A autoantibodies in a human biological specimen comprising a container; instructional material: a labeled binding agent capable of binding said anti-Ro/SS-A antibodies; and cells from a HEp-2 cell line stably transfected with a recombinant expression cassette comprising a nucleic acid encoding a human Ro/SS-A autoantigen, wherein said transfected HEp-2 cell line overexpresses said Ro/SS-A autoantigen, and wherein said autoantibodies are capable of binding to said Ro/SS-A autoantigen in said cells to form an autoantigen:autoantibody complex.

18. The kit of claim 17 wherein said Ro/SS-A autoantigen is 60 kd Ro/SS-A.

19. The kit of claim 17 wherein said Ro/SS-A autoantigen is 52 kd Ro/SS-A.

20. The kit of claim 17 wherein said labeled binding agent is a fluorescent-labeled binding agent.

21. The kit of claim 17 wherein said HEp-2 cell line is HEp/Ro 60.

22. The kit of claim 17 wherein said HEp-2 cell line is HEp/Ro 52.

23. The kit of claim 17 wherein said recombinant expression cassette further comprises a human cytomegalovirus immediate early promoter.

* * * * *